(12) United States Patent
Takamatsu et al.

(10) Patent No.: US 9,706,973 B2
(45) Date of Patent: Jul. 18, 2017

(54) MEDICAL IMAGE PROCESSING APPARATUS AND X-RAY COMPUTED TOMOGRAPHY APPARATUS

(71) Applicant: Toshiba Medical Systems Corporation, Otawara-shi (JP)

(72) Inventors: Yuko Takamatsu, Utsunomiya (JP); Hiroki Taguchi, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/630,220

(22) Filed: Feb. 24, 2015

(65) Prior Publication Data
US 2015/0164456 A1 Jun. 18, 2015

Related U.S. Application Data

(63) Continuation of application No. PCT/JP2013/072771, filed on Aug. 26, 2013.

(30) Foreign Application Priority Data

Aug. 30, 2012 (JP) .................................. 2012-190237
Aug. 26, 2013 (JP) .................................. 2013-174909

(51) Int. Cl.
*A61B 6/00* (2006.01)
*A61B 6/03* (2006.01)
*G06T 11/00* (2006.01)

(52) U.S. Cl.
CPC ............. *A61B 6/5258* (2013.01); *A61B 6/032* (2013.01); *A61B 6/482* (2013.01); *A61B 6/5205* (2013.01); *G06T 11/006* (2013.01)

(58) Field of Classification Search
CPC ...... A61B 6/5258; A61B 6/482; A61B 6/5205; A61B 6/032; G06T 11/006
(Continued)

(56) References Cited

U.S. PATENT DOCUMENTS 6,266,388 B1    7/2001 Hsieh
7,623,691 B2    11/2009 Hein et al.
(Continued)

FOREIGN PATENT DOCUMENTS

DE    WO 2013124777 A1 *  8/2013  ............. A61B 6/032
JP         60-181640 A       9/1985
(Continued)

OTHER PUBLICATIONS

International Search Report mailed Nov. 26, 2013 for PCT/JP2013/072771 filed on Aug. 26, 2013 with English Translation.
(Continued)

*Primary Examiner* — Amandeep Saini
(74) *Attorney, Agent, or Firm* — Oblon, McClelland, Maier & Neustadt, L.L.P.

(57) ABSTRACT

A medical image processing apparatus according to an embodiment includes a separating unit, a reconstructing unit, and an extracting unit. The separating unit separates projection data into pieces of line-integrated data each of which corresponds to a different one of basis materials set in advance. The reconstructing unit reconstructs pieces of basis material image data from the pieces of line-integrated data each of which corresponds to a different one of the basis materials, the pieces of basis material image data being configured so that each pixel value of each of pixels indicates an abundance ratio of corresponding each of the basis materials that is present at each of the pixel. The extracting unit extracts an artifact region, on a basis of attenuation coefficients of each of the pixels calculated from the pieces of basis material image data each of which corresponds to a different one of the basis materials.

13 Claims, 6 Drawing Sheets

(58) Field of Classification Search
USPC .......................................................... 382/131
See application file for complete search history.

(56) References Cited

U.S. PATENT DOCUMENTS

| | | | |
|---|---|---|---|
| 7,876,874 B2 | 1/2011 | Goto et al. | |
| 7,953,263 B2 | 5/2011 | Okamoto et al. | |
| 8,194,961 B2 | 6/2012 | Zou et al. | |
| 2009/0262997 A1* | 10/2009 | Zou ....................... | G06T 11/005 382/131 |
| 2012/0093279 A1* | 4/2012 | Akino .................... | A61B 6/032 378/5 |

FOREIGN PATENT DOCUMENTS

| | | |
|---|---|---|
| JP | 2001-137228 A | 5/2001 |
| JP | 2006-043431 A | 2/2006 |
| JP | 2006-320464 A | 11/2006 |
| JP | 2009-047602 A | 3/2009 |
| JP | 2009-261942 A | 11/2009 |
| WO | WO 2006/057304 A1 | 6/2006 |

OTHER PUBLICATIONS

International Written Opinion mailed Nov. 26, 2013 for PCT/JP2013/072771 filed on Aug. 26, 2013.

\* cited by examiner

MEDICAL IMAGE PROCESSING APPARATUS AND X-RAY COMPUTED TOMOGRAPHY APPARATUS

CROSS-REFERENCE TO RELATED APPLICATIONS

This application is a continuation of International Application No. PCT/JP2013/072771, filed on Aug. 26, 2013 which claims the benefit of priority of the prior Japanese Patent Application No. 2012-190237, filed on Aug. 30, 2012 and Japanese Patent Application No. 2013-174909, filed on Aug. 26, 2013, the entire contents of which are incorporated herein by reference.

FIELD

Embodiments described herein relate generally to a medical image processing apparatus and an X-ray computed tomography apparatus.

BACKGROUND

Conventionally, a method for obtaining images is known by which image taking processing is performed by an X-ray Computed Tomography (CT) apparatus while using multi different levels of X-ray tube voltages. When two mutually-different levels of X-ray tube voltages are used, the method may be called a "dual-energy CT" method. In "dual-energy CT", two projection data obtained from two mutually-different levels of X-ray tube voltages are separated into projection data (line-integrated data) each corresponding to respective predetermined two basis materials, and from each of the two separated data, image based on the abundance ratio of the basis materials (basis material image) is reconstructed, the above-described which applied technology is known. According to such applied technology, it is possible to obtain various types of images such as a monochromatic X-ray image, a density image, an effective atomic number image, and the like, by performing a weighted calculation while using the two basis material images.

The applied technology described above is effective in correcting artifacts caused by beam hardening. However, besides the artifacts caused by beam hardening, there are other various artifacts such as those caused by a degradation in the precision level of the projection data due to highly-absorbent materials and those caused by scattered rays.

In particular, artifacts often occur due to a degradation in the precision level of the projection data caused by highly-absorbent materials. The reason can be explained as follows: When a material (e.g., metal) having a large linear absorption coefficient is present in an image taking target, the count of a detector shows a very small value during an image taking processing using a low level of X-ray tube voltage, and it is therefore not possible to obtain proper projection data. In that situation, it is not possible to properly obtain the projection data of the basis materials. As a result, the acquired monochromatic X-ray image will have an artifact where, for example, information in the surroundings of the highly-absorbent material is missing. According to the applied technology described above, it is not possible to generate a monochromatic X-ray image from which the impacts of the artifacts other than the artifacts caused by beam hardening are also eliminated.

DETAILED DESCRIPTION

A medical image processing apparatus according to an embodiment includes a separating unit, a reconstructing unit, and an extracting unit. The separating unit separates projection data into pieces of line-integrated data each of which corresponds to a different one of a plurality of basis materials that are set in advance. The reconstructing unit reconstructs pieces of basis material image data from the pieces of line-integrated data each of which corresponds to a different one of the plurality of basis materials. the pieces of basis material image data being configured so that each pixel value of each of pixels indicates an abundance ratio of corresponding each of the basis materials that is present at each of the pixel. The extracting unit extracts an artifact region, on a basis of attenuation coefficients of each of the pixels calculated from the pieces of basis material image data each of which corresponds to a different one of the plurality of basis materials.

Exemplary embodiments of a medical image processing apparatus will be explained in detail below, with reference to the accompanying drawings. In the following sections, an X-ray computed tomography (CT) apparatus that functions as the medical image processing apparatus will be explained in the exemplary embodiments.

(First Embodiment)

Figure 1:
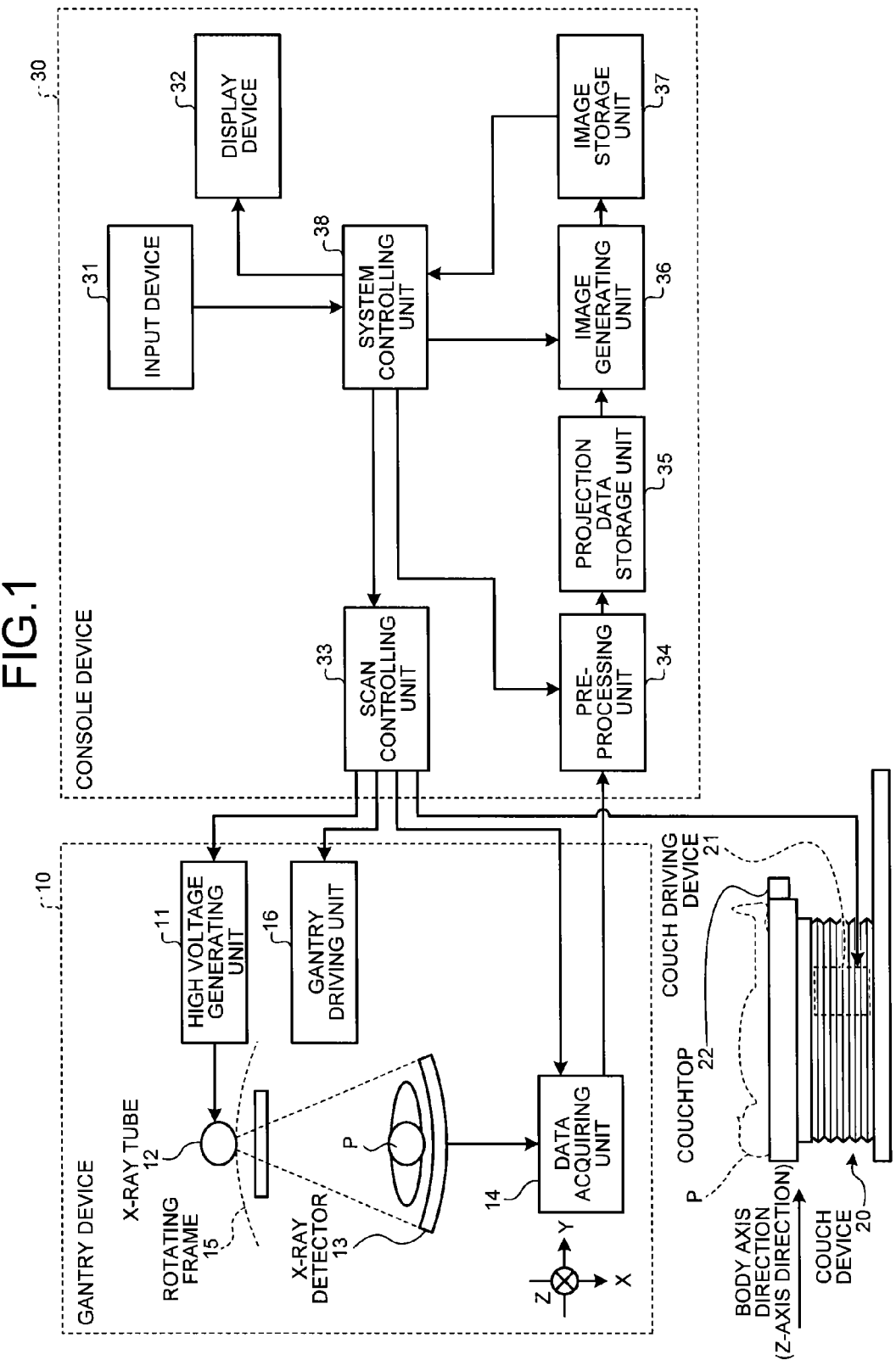
FIG. 1 is a diagram of an exemplary overall configuration of an X-ray CT apparatus according to a first embodiment.

First, an exemplary overall configuration of an X-ray CT apparatus according to a first embodiment will be explained, with reference to FIG. 1. FIG. 1 is a diagram of the exemplary overall configuration of the X-ray CT apparatus according to the first embodiment. As shown in FIG. 1, the X-ray CT apparatus according to the first embodiment includes a gantry device 10, a couch device 20, and a console device 30.

The gantry device 10 is a device configured to radiate X-rays onto an examined subject (hereinafter, a "subject") P and to acquire X-ray detection data and includes a high voltage generating unit 11, an X-ray tube 12, an X-ray detector 13, a data acquiring unit 14, a rotating frame 15, and a gantry driving unit 16.

The high voltage generating unit 11 is a device configured to generate a high voltage and to supply the generated high voltage to the X-ray tube 12. The X-ray tube 12 is a vacuum tube that generates X-rays with the high voltage supplied from the high voltage generating unit 11. The X-rays generated by the X-ray tube 12 are radiated onto the subject P.

The X-ray detector 13 is a detector that detects the X-ray detection data indicating an intensity distribution of the X-rays that were radiated from the X-ray tube 12 and have passed through the subject P. In other words, the X-ray detector 13 detects the X-ray detection data indicating a degree of X-ray absorption occurring inside the body of the subject P. For example, the X-ray detector 13 is a two-dimensional array detector in which a plurality of rows of detecting elements are arranged along the body axis direction of the subject P (i.e., the Z-axis direction shown in FIG. 1), each row of detecting elements being made up of a plurality of X-ray detecting elements that are arranged along the channel direction (i.e., the Y-axis direction shown in FIG. 1).

The rotating frame 15 supports the X-ray tube 12 and the X-ray detector 13 in such a manner that the X-ray tube 12 and the X-ray detector 13 oppose each other while the subject P is interposed therebetween. The gantry driving unit 16 is a driving device that causes the X-ray tube 12 and the X-ray detector 13 to revolve on a circular orbit centered about the subject P, by driving the rotating frame 15 to rotate.

The data acquiring unit 14 is a Data Acquisition System (DAS) and acquires the X-ray detection data detected by the X-ray detector 13. More specifically, the data acquiring unit 14 acquires the X-ray detection data corresponding to each of the directions (hereinafter, "X-ray radiation directions") in which the X-rays are radiated from the X-ray tube 12. The X-ray radiation directions may be referred to as "views". Furthermore, the data acquiring unit 14 performs an amplifying processing and/or an Analog/Digital (A/D) conversion processing on the acquired X-ray detection data corresponding to each of the views and outputs the result to a pre-processing unit 34 (explained later) included in the console device 30. For example, the data acquiring unit 14 outputs data (sinogram data) obtained by arranging the X-ray detection data in a time-series manner for each of the X-ray radiation directions, the X-ray detection data indicating an X-ray detection amount for each of the X-ray detecting elements.

The couch device 20 is a device on which the subject P is placed. As shown in FIG. 1, the couch device 20 includes a couchtop 22 and a couch driving device 21. The couchtop 22 is a bed on which the subject P is placed. The couch driving device 21 moves the subject P into the inside of the rotating frame 15, by moving the couchtop 22 along the body axis direction of the subject P (i.e., the Z-axis direction).

The console device 30 is a device that receives operations performed on the X-ray CT apparatus by an operator and to reconstruct a tomography image from a group of data acquired by the gantry device 10. As shown in FIG. 1, the console device 30 includes an input device 31, a display device 32, a scan controlling unit 33, the pre-processing unit 34, a projection data storage unit 35, an image generating unit 36, an image storage unit 37, and a system controlling unit 38.

The input device 31 includes a mouse, a keyboard, a button, a trackball, a joystick, and/or the like that are used for inputting various types of instructions by the operator such as a medical doctor or a technician who operates the X-ray CT apparatus and transfers various types of commands received from the operator to the system controlling unit 38 (explained later).

The display device 32 includes a monitor that displays a Graphical User Interface (GUI) used for receiving an instruction from the operator via the input device 31 and to display images stored in the image storage unit 37 (explained later).

The scan controlling unit 33 controls operations of the high voltage generating unit 11, the gantry driving unit 16, the data acquiring unit 14, and the couch driving device 21. Thus, the scan controlling unit 33 controls an X-ray scanning processing performed on the subject P by the gantry device 10, as well as an acquiring processing of a group of X-ray detection data and a data processing performed on the group of X-ray detection data.

More specifically, the scan controlling unit 33 causes an X-ray scan to be performed by causing X-rays to be radiated continuously or intermittently from the X-ray tube 12, while causing the rotating frame 15 to rotate. For example, the scan controlling unit 33 causes a helical scan to be performed so that images are taken by causing the rotating frame 15 to rotate continuously while the couchtop 22 is being moved or causes a conventional scan to be performed so that images are taken by causing the rotating frame 15 to rotate with a single complete cycle or continuously, while the position of the subject P is fixed.

The pre-processing unit 34 generates projection data by performing a logarithmic conversion processing and a correcting processing such as an offset correcting processing or a sensitivity correcting processing, on the X-ray detection data transmitted from the data acquiring unit 14. Processing performed by the pre-processing unit 34 according to the first embodiment will be explained in detail later.

The projection data storage unit 35 stores therein the projection data generated by the pre-processing unit 34.

The image generating unit 36 generates various types of images from the projection data stored in the projection data storage unit 35 and to store the generated images into the image storage unit 37. For example, the image generating unit 36 reconstructs an X-ray CT image by performing a back-projection processing (e.g., a back-projection processing realized by implementing a Filtered Back Projection (FBP) method) on the projection data and stores the reconstructed X-ray CT image into the image storage unit 37. Processing performed by the image generating unit 36 according to the first embodiment will be explained in detail later.

The system controlling unit 38 exercises overall control of the X-ray CT apparatus, by controlling operations of the gantry device 10, the couch device 20, and the console device 30. More specifically, by controlling the scan controlling unit 33, the system controlling unit 38 controls the acquiring processing of the group of X-ray detection data performed by the gantry device 10 and the couch device 20. Furthermore, by controlling the pre-processing unit 34 and the image generating unit 36, the system controlling unit 38 controls image processing performed by the console device 30. Furthermore, the system controlling unit 38 exercises control so that the various types of images stored in the image storage unit 37 are displayed on the display device 32.

The overall configuration of the X-ray CT apparatus according to the first embodiment has thus been explained. In addition to acquiring projection data by performing an image taking processing while the X-ray tube voltage is fixed to one level, the X-ray CT apparatus according to the first embodiment configured as described above also acquires projection data by performing a "multi-energy image taking processing" while using multi different levels of X-ray tube voltages. For example, the X-ray CT apparatus according to the first embodiment acquires the projection data by performing a "dual-energy image taking processing" while using two mutually-different levels of X-ray tube voltages.

The "dual-energy image taking processing" may be performed, for example, by implementing any of the following three image taking methods. A first image taking method is called a "slow-kV switching method (two-rotation method)" by which an image taking processing is performed at first by using a first X-ray tube voltage, and subsequently, an image taking processing is performed by using a second X-ray tube voltage. A second image taking method is called a "dual source method (two-tube method)" by which an image taking processing is performed while using mutually-different X-ray tube voltages, with the use of a two-tube X-ray CT apparatus, instead of the one-tube X-ray CT apparatus shown in FIG. 1. A third image taking method is called a "fast-kV switching method (a high-speed switching method)" by which an image taking processing is performed by switching X-ray tube voltages at a high speed in correspondence with each of the views, while causing the rotating frame 15 to rotate. By using any of these methods, it is possible to obtain two types of raw data (projection data) having mutually-different energy levels.

In the following sections, an example will be explained in which the "dual-energy image taking processing" is performed by implementing the high-speed switching method. The first embodiment is also applicable to situations where the "dual-energy image taking processing" is performed by implementing the two-rotation method or the two-tube method.

In recent years, applied technology has been developed by which two pieces of projection data obtained by using two mutually-different levels of X-ray tube voltages are separated into pieces of projection data (line-integrated data) each of which corresponds to a different one of two basis materials that are set in advance, so that an image (hereinafter, a "basis material image") based on the abundance ratio of each of the two basis materials is reconstructed. According to this applied technology, it is possible to obtain various types of images such as a monochromatic X-ray image, a density image, an effective atomic number image, and the like, by performing a weighted calculation while using the two basis material images.

The applied technology described above is effective in correcting artifacts caused by beam hardening. For example, it is possible to generate an X-ray CT image of monochromatic X-rays (a monochromatic X-ray image or a monochromatic X-ray CT image) in which the impact of beam hardening is reduced compared to that in a conventional X-ray CT image of continuous X-rays. However, besides the artifacts caused by beam hardening, there are other various artifacts such as those caused by a degradation in the precision level of the projection data due to highly-absorbent materials and those caused by scattered rays.

According to the applied technology described above, it is not possible to generate a monochromatic X-ray image from which the impacts of the artifacts other than the artifacts caused by beam hardening are also eliminated. To cope with this situation, according to the first embodiment, processing described below are performed by the pre-processing unit 34 and the image generating unit 36, so as to extract artifacts occurring in a monochromatic-X-ray image.

Figure 2:
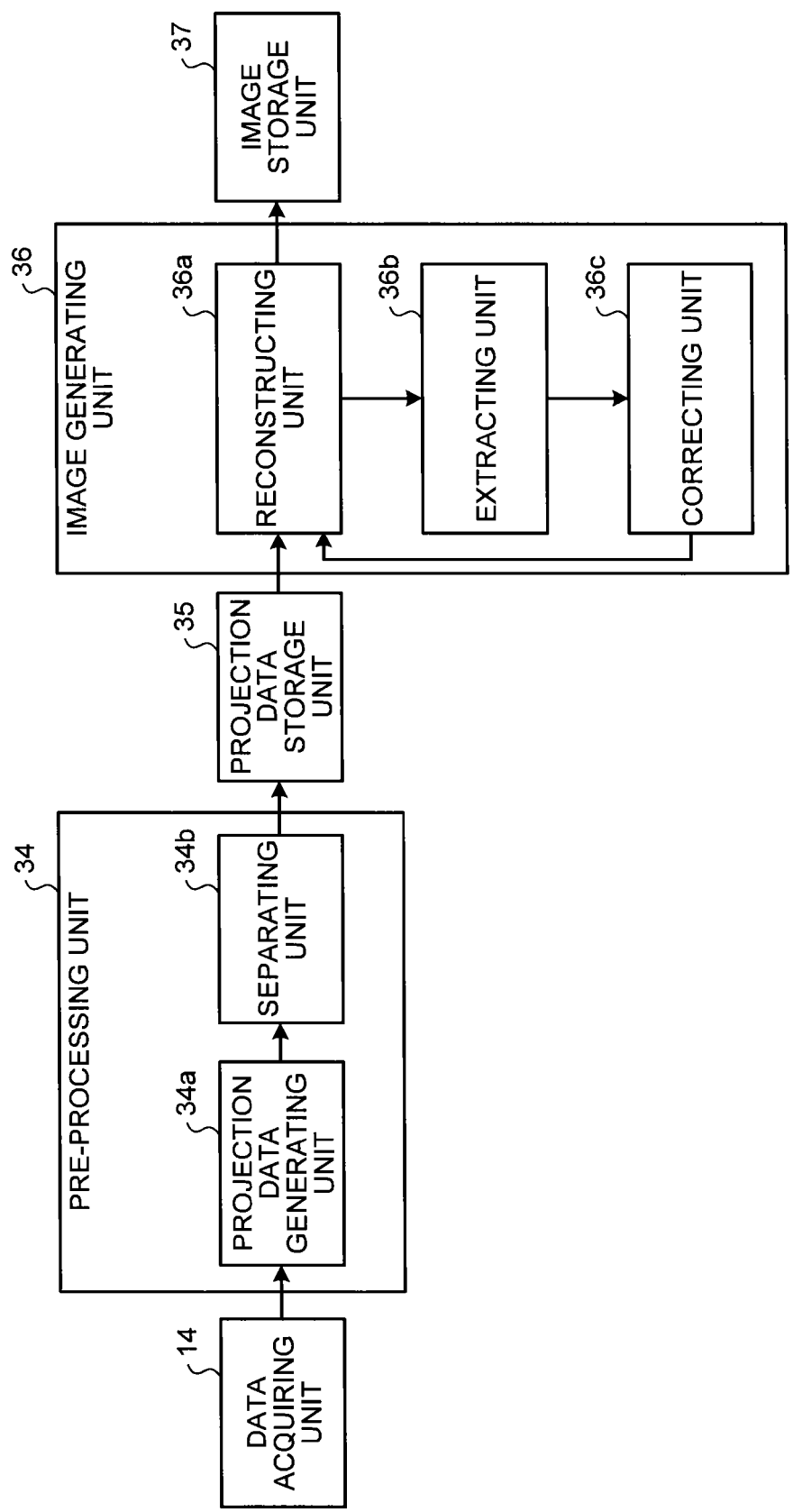
FIG. 2 is a diagram of exemplary configurations of a pre-processing unit and an image generating unit according to the first embodiment.

FIG. 2 is a diagram of exemplary configurations of the pre-processing unit and the image generating unit according to the first embodiment. As shown in FIG. 2, the pre-processing unit 34 according to the first embodiment includes a projection data generating unit 34a and a separating unit 34b. Furthermore, as shown in FIG. 2, the image generating unit 36 according to the first embodiment includes a reconstructing unit 36a, an extracting unit 36b, and a correcting unit 36c.

The projection data generating unit 34a generates the projection data by performing a logarithmic conversion processing or the like on the X-ray detection data transmitted from the data acquiring unit 14. In the first embodiment, the projection data generating unit 34a generates projection data (hereinafter, "high energy projection data") from X-ray detection data obtained by using a first X-ray tube voltage (e.g., 130 kV). Furthermore, in the first embodiment, the projection data generating unit 34a generates projection data (hereinafter, "low energy projection data") from X-ray detection data obtained by using a second X-ray tube voltage (e.g., 80 kV).

The separating unit 34b separates the projection data into pieces of line-integrated data each of which corresponds to a different one of a plurality of basis materials (i.e., two or more basis materials) that are set in advance. In the first embodiment, the projection data is represented by two pieces of projection data (the high energy projection data and the low energy projection data) acquired by using two mutually-different levels of X-ray tube voltages.

Furthermore, in the first embodiment, the plurality of basis materials are two basis materials, which are, for example, bones and water. In the following sections, one of the two basis materials will be referred to as a first basis material, whereas the other will be referred to as a second basis material.

More specifically, the separating unit 34b separates the high energy projection data and the low energy projection data into line-integrated data (first line-integrated data) of the first basis material and line-integrated data (second line-integrated data) of the second basis material. In this situation, the basis materials are specified out of materials of which the mass attenuation coefficients at various levels of energy are known.

The first line-integrated data and the second line-integrated data separated by the separating unit 34b are stored into the projection data storage unit 35.

Furthermore, the reconstructing unit 36a reconstructs pieces of basis material image data from the pieces of line-integrated data each of which corresponds to a different one of the plurality of basis materials, the pieces of basis material image data being configured so that each pixel value of each of pixels (or the voxels) indicates an abundance ratio of corresponding each of the basis materials that is present at each of the pixel. More specifically, by performing a back-projection processing on the first line-integrated data, the reconstructing unit 36a reconstructs basis material image data (hereinafter, "first basis material image data") of the first basis material. Furthermore, by performing a back-projection processing on the second line-integrated data, the reconstructing unit 36a reconstructs basis material image data (hereinafter, "second basis material image data") of the second basis material. In this situation, the pixel value of a pixel "i" in the first basis material image data indicates the abundance ratio "$c_1$" of the first basis material at the pixel "i". Similarly, the pixel value of a pixel "i" in the second basis material image data indicates the abundance ratio "$c_2$" of the second basis material at the pixel "i".

In this situation, the attenuation coefficient "$\mu(E)$" in an image taking site corresponding to the pixel "i" at an arbitrary level of energy "E" can be calculated by using Expression (1) shown below. In Expression (1) below, "$\mu_1(E)$" denotes the attenuation coefficient for the first basis material at "E", whereas "$\mu_2(E)$" denotes the attenuation coefficient for the second basis material at "E".

$$\mu(E)=c_1\mu_1(E)+c_2\mu_2(E) \tag{1}$$

The CT value "CT#(E)" of the image taking site corresponding to the pixel "i" at "E" can be calculated by assigning the value "μ(E)" calculated from Expression (1) and an attenuation coefficient "μ(E)" of water at "E" to Expression (2) shown below.

$$CT\#(E) = 1000 \times \frac{\mu(E) - \mu_w(E)}{\mu_w(E)} \quad (2)$$

The reconstructing unit 36a is thus able to generate a monochromatic X-ray image at the arbitrary level of energy "E", by using the basis material image data and Expressions (1) and (2). In the attenuation coefficient calculated from Expression (1), the error caused by beam hardening is reduced. However, the attenuation coefficient calculated from Expression (1) still has, for example, impacts of metal artifacts, artifacts caused by bones and a contrast agent, and cone beam artifacts.

Figure 3:
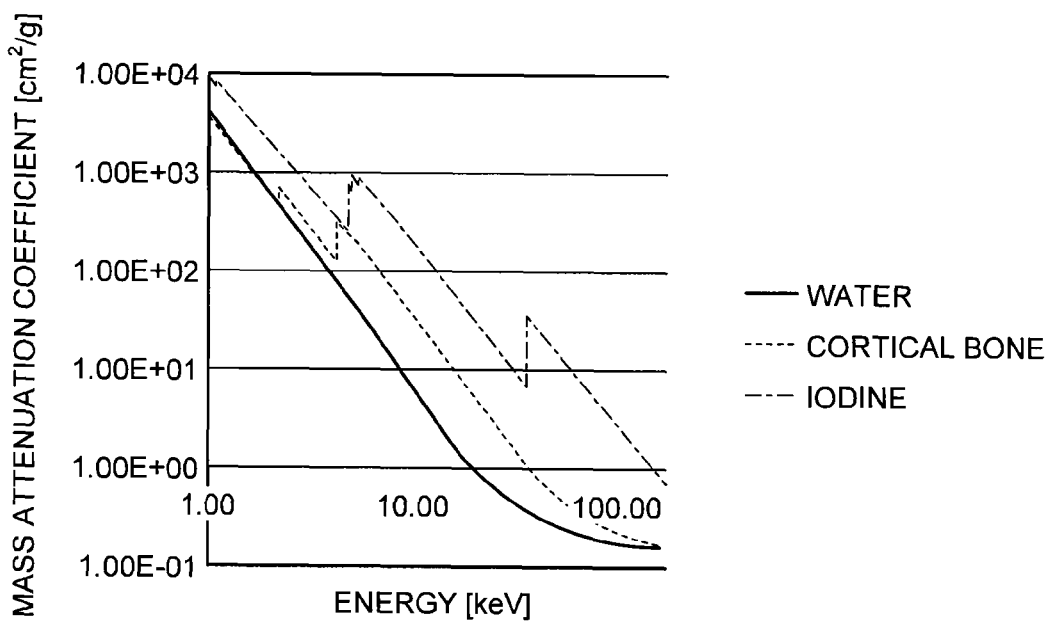
FIG. 3 is a chart for explaining an extracting unit according to the first embodiment.

To cope with this situation, the extracting unit 36b shown in FIG. 2 extracts an artifact region, on a basis of the attenuation coefficients of each of the pixels calculated from the pieces of basis material image data each of which corresponds to a different one of the plurality of basis materials. The extracting unit 36b according to the first embodiment extracts the artifact region by comparing attenuation coefficients at two mutually-different energy levels with each other, within an energy range that does not include absorption edge energies. FIG. 3 is a chart for explaining the extracting unit according to the first embodiment.

By using Expression (1), the extracting unit 36b according to the first embodiment calculates an attenuation coefficient for each of the pixels at each of the two energy levels ($E_1$ and $E_2$). As for the magnitude relationship between the two levels of energy, "$E_1 < E_2$" is satisfied. In this situation, the mass attenuation coefficient (the linear attenuation coefficient/density) of each of the materials exhibits a formation as shown in FIG. 3, in relation to the photon energy. In FIG. 3, the mass attenuation coefficient of water is indicated with a solid line, whereas the mass attenuation coefficient of bones (cortical bones) is indicated with a broken line, while the mass attenuation coefficient of iodine is indicated with a dot-and-dash line.

As shown in FIG. 3, in energy regions where the photoelectric effect or the Compton scattering is dominant, "$\mu(E_1) > \mu(E_2)$" is satisfied for any material, except in the region near the absorption edge energies where the attenuation coefficient is discontinuous. On a basis of this fact, the extracting unit 36b determines that correct values of "$c_1$" and "$c_2$" are not obtained at such a pixel where "$\mu(E_1) > \mu(E_2)$" is not satisfied and thus extracts such a pixel as an artifact region. In other words, if the magnitude relationship between the attenuation coefficients at the two mutually-different energy levels calculated from "$c_1$" and "$c_2$" of a given pixel exhibits a physical contradiction, the extracting unit 36b determines that the pixel is in an artifact region.

The two levels of energy can be set by the operator within a range that excludes the absorption edge energies of each of the two basis materials that have been set. Alternatively, the two levels of energy may be configured into the apparatus in advance as an initial setting, in accordance with the pair made up of the basis materials. Alternatively, the two levels of energy may be set by the extracting unit 36b in accordance with the pair made up of the basis materials.

After that, the correcting unit 36c shown in FIG. 2 corrects the attenuation coefficients of the artifact region. For example, the correcting unit 36c corrects the attenuation coefficients of the artifact region by utilizing the following notion: the values "$c_1$" and "$c_2$" in the artifact region are incorrect; however, among the attenuation coefficients at various levels of energy calculated from the incorrect values of "$c_1$" and "$c_2$", an attenuation coefficient obtained at a certain level of energy "E_cor" has a correct value.

In the range from which the absorption edge energies are excluded, the value of a correct attenuation coefficient becomes smaller, as the level of energy becomes higher. In other words, a chart of a correct attenuation coefficient has a formation that falls toward the right. In contrast, the attenuation coefficient of the artifact region extracted in the first embodiment becomes larger as the level of energy becomes higher, even in the region excluding the absorption edge energies. In other words, a chart of the attenuation coefficient of the artifact region has a formation that rises toward the right. The chart of the correct attenuation coefficient having the formation that falls toward the right intersects, at a certain point, the chart of the attenuation coefficient of the artifact region having the formation that rises toward the right. The level of energy at the intersecting point serves as "E_cor" mentioned above.

Thus, the correcting unit 36c obtains an energy level "E_cor" at which each of the attenuation coefficients of the artifact region calculated from pixel values in the pieces of basis material image data each of which corresponds to a different one of the plurality of basis materials exhibits a substantially correct value. In the first embodiment, the correcting unit 36c obtains the level of energy "E_cor" at which each of the attenuation coefficients of the artifact region calculated from the pixel values in each of the first and the second basis material image data exhibits a substantially correct value. Furthermore, the correcting unit 36c performs a correcting processing by using each of the attenuation coefficients of the artifact region at "E_cor" and the attenuation coefficient of predetermined materials at "E_cor".

For example, as "E_cor", the correcting unit 36c obtains an energy value that is empirically or experimentally calculated in advance. In that situation, for example, the value of "E_cor" is configured into the system controlling unit 38 as an initial setting, so that the correcting unit 36c obtains "E_cor" from the system controlling unit 38. Alternatively, the value of "E_cor" may be set by the operator via the input device 31, when the correcting unit 36c performs the processing. In that situation, the correcting unit 36c obtains "E_cor" that has been set through the input device 31, via the system controlling unit 38.

The level of energy "E_cor" at which it is possible to obtain a correct attenuation coefficient is not necessarily always the same. For this reason, in the first embodiment, a correlation between the attenuation coefficient "μ(A)" at a certain level of energy "A" and "E_cor" is calculated in advance. In this situation, "A" denotes a level of energy that is set in advance in accordance with the pair made up of the basis materials, within the range that excludes the absorption edge energies. "μ(A)" is a value that can be calculated by assigning "$c_1$" and "$c_2$", the attenuation coefficient of the first basis material at "A" and the attenuation coefficient of the second basis material at "A" to Expression (1).

As an example, the first embodiment utilizes the fact that "E_cor" and "μ(A)" satisfy a relationship of a linear function such as Expression (3) shown below that is expressed with a slope "a" and a Y-intercept "b".

$$E\_cor = a \times \mu(A) + b \quad (3)$$

In this situation, "A", "a", and "b" are values that can be obtained experimentally. Furthermore, in the first embodiment, the example is explained in which the relationship between "E_cor" and "μ(A)" is expressed with the linear function; however, the relationship between "E_cor" and "μ(A)" may be expressed with any of other various functions such as a polynomial function, an exponential function, or a logarithmic function. Furthermore, as mentioned above, when the correcting processing is performed while the value of "E_cor" is set to a constant value, it means that Expression (3) is set so as to satisfy "a=0; b=E_cor".

The correcting unit 36c calculates "E_cor" by assigning "μ(A)" calculated from "$c_1$" and "$c_2$" of the pixel extracted as an artifact region to Expression (3). After that, the correcting unit 36c calculates an attenuation coefficient "μ(E_cor)" at "E_cor", by assigning the attenuation coefficient of the first basis material, the attenuation coefficient of the second basis material, and "$c_1$" and "$c_2$" at "E_cor" to Expression (1). The attenuation coefficient "μ(E_cor)" is the attenuation coefficient of the artifact region at "E_cor" and can be used as a value that approximates the true attenuation coefficient of the artifact region at "E_cor".

After that, the correcting unit 36c performs the correcting processing by using the attenuation coefficient "μ(E_cor)" and the attenuation coefficient of a predetermined material at "E_cor". For example, the predetermined material may be water. In that situation, the correcting unit 36c assigns an attenuation coefficient "$\mu_w(E)$" of water at the energy level "E" corresponding to a monochromatic X-ray image, an attenuation coefficient "$\mu_w(E\_cor)$" of water at "E_cor", and "μ(E_cor)" to Expression (4) shown below. As a result, the correcting unit 36c is able to obtain an attenuation coefficient "μ'(E)" after the correction (hereinafter, "corrected attenuation coefficient") of the pixel extracted as an artifact region.

$$\mu'(E) = \mu(\text{E\_cor}) \times \frac{\mu_w(E)}{\mu_w(\text{E\_cor})} \quad (4)$$

In Expression (4) above, the attenuation coefficient of water is used; however, the first embodiment may be configured so that a corrected attenuation coefficient is calculated by using an attenuation coefficient of any other appropriate material. In this situation, even if the correcting processing is performed by setting "E_cor" to a constant value, it is possible to obtain a corrected attenuation coefficient of the artifact region by using Expression (4) above.

Figure 4:
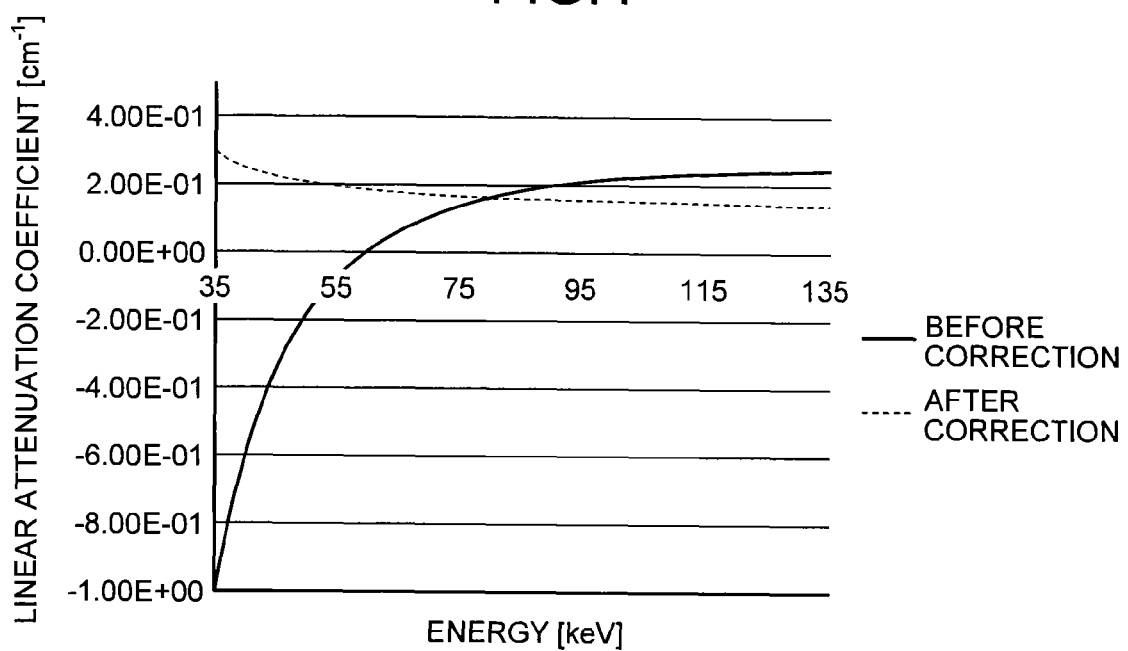
FIG. 4 is a chart of an example of processing results obtained by a correcting unit according to the first embodiment.

FIG. 4 is a chart of an example of processing results obtained by the correcting unit according to the first embodiment. In FIG. 4, a chart of an attenuation coefficient (a linear attenuation coefficient) before the correction (hereinafter, a "pre-correction attenuation coefficient") of the artifact region is indicated with a solid line, whereas a chart of an attenuation coefficient (a linear attenuation coefficient) after the correction (a "corrected attenuation coefficient") of the artifact region is indicated with a broken line. As a result of the correcting processing by the correcting unit 36c, the chart of the pre-correction attenuation coefficient, which has a formation that rises toward the right, changes to the chart having a formation that falls toward the right, which exhibits no physical contradiction, as shown in FIG. 4.

The reconstructing unit 36a shown in FIG. 2 generates a monochromatic X-ray image by using the corrected attenuation coefficients. More specifically, for the artifact region, the reconstructing unit 36a calculates CT values by assigning the corrected attenuation coefficients to Expression (2). Furthermore, for the region other than the artifact region, the reconstructing unit 36a calculates CT values by calculating an attenuation coefficient from each of the pixel values in the first basis material image data and the second basis material image data by using Expression (1) and further assigning the calculated attenuation coefficient to Expression (2). Thus, the reconstructing unit 36a generates the monochromatic X-ray image at the energy level "E".

After that, under the control of the system controlling unit 38, the display device 32 displays the monochromatic X-ray image at the energy level "E".

Figure 5:
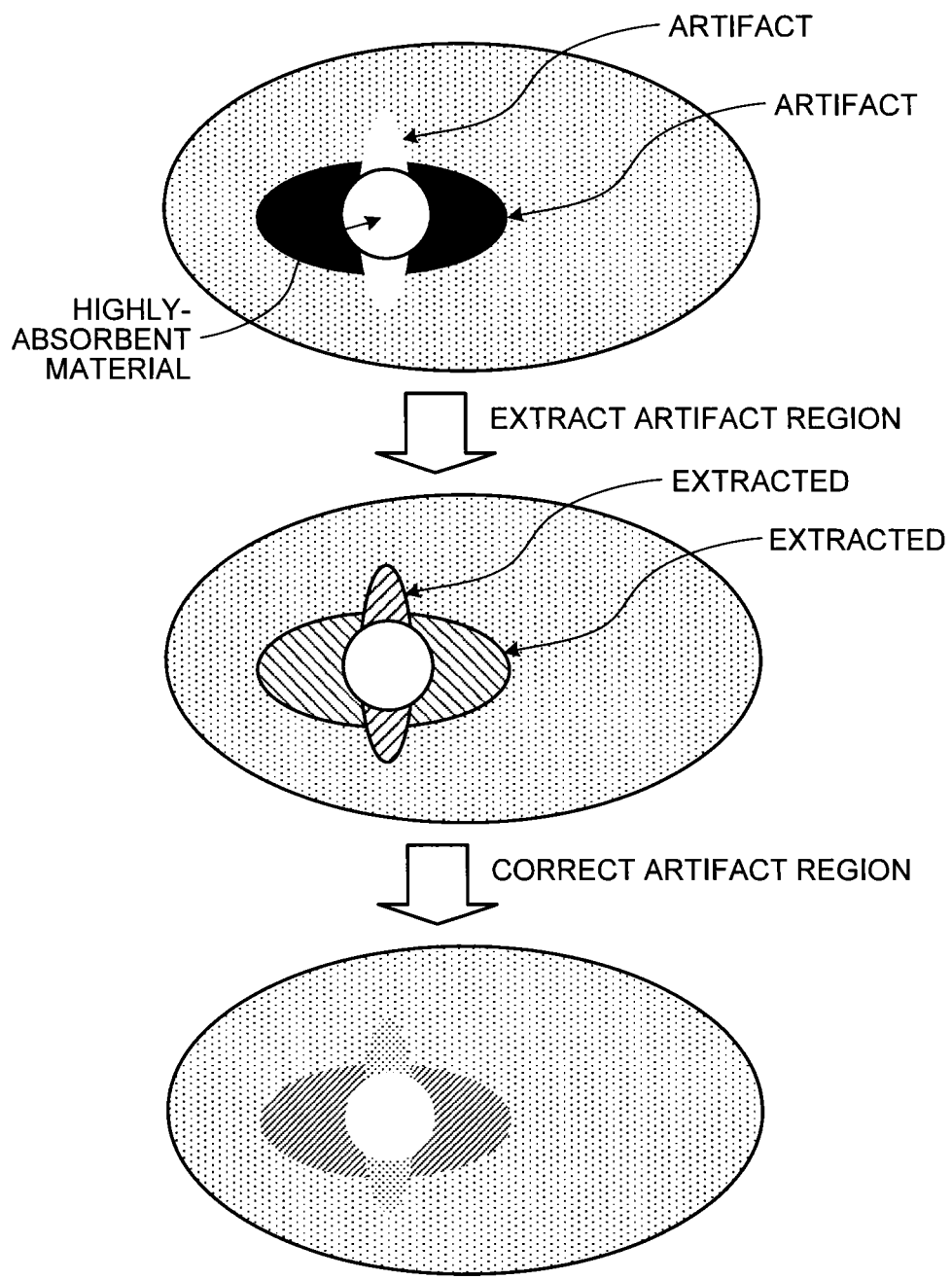
FIG. 5 is a drawing of a contour of processing according to the first embodiment.

FIG. 5 is a drawing of a contour of processing according to the first embodiment. As shown in the top part of FIG. 5, when the correcting processing by the correcting unit 36c has not been performed, a white artifact and a black artifact occur in the monochromatic X-ray image due to a degradation in the precision level of the projection data caused by highly-absorbent materials.

As shown in the middle part of FIG. 5, all of such a region is extracted as an artifact region, as a result of the extracting processing by the extracting unit 36b. After that, as shown in the bottom part of FIG. 5, as a result of the correcting processing by the correcting unit 36c, a monochromatic X-ray image is generated in which the artifact region caused by the highly-absorbent materials has been corrected.

When the correcting processing is performed while the value of "E_cor" is set to a constant value, it is acceptable for the operator to change the value of "E_cor". For example, the operator may refer to the monochromatic X-ray image generated by using the corrected attenuation coefficient of the artifact region at the energy level "E" and may change the value of "E_cor" if the operator has determined that the correction of the monochromatic X-ray image was not properly performed. In that situation, the correcting unit 36c performs the correcting processing on the attenuation coefficient again by using the value "E_cor" that has been changed, so that the reconstructing unit 36a generates a monochromatic X-ray image by using the attenuation coefficient that has been corrected again. Furthermore, when the correcting processing is performed while the value of "E_cor" is set to a constant value, it is also acceptable to set a plurality of values each as "E_cor", so as to perform a correcting processing by using each of the plurality of values and to generate a plurality of monochromatic X-ray images. In that situation, the operator is able to, for example, select a monochromatic X-ray image in which the artifacts have properly been reduced, from among the plurality of monochromatic X-ray images. Furthermore, even in the situation where "E_cor" is obtained by using Expression (3) and where the attenuation coefficient of the artifact region is corrected by using "E_cor" obtained from Expression (3) as well as Expression (4), the operator may perform the processing of changing the value of "E_cor".

Furthermore, the first embodiment may be configured so that a correcting processing is performed through any of the following processing in which Expression (3) and (4) are not used. For example, the correcting unit 36c may perform a correcting processing by replacing each of the attenuation coefficients of the artifact region with attenuation coefficients of predetermined materials. In that situation, the correcting unit 36c performs the correcting processing by replacing each of the attenuation coefficients of the artifact region with an attenuation coefficient of an arbitrary material. The arbitrary material may be, for example, a soft tissue.

Alternatively, the correcting unit 36c may correct each of the attenuation coefficients of the artifact region by applying a correcting processing on the projection data or the line-integrated data that passes through the artifact region. For example, the correcting unit 36c corrects the high energy projection data and the low energy projection data that pass through the artifact region, so that the separating unit 34b is caused to separate, again, the corrected projection data into first line-integrated data and second line-integrated data. Alternatively, for example, the correcting unit 36c corrects the first line-integrated data and the second line-integrated data that pass through the artifact region. After that, the correcting unit 36c causes the reconstructing unit 36a to reconstruct basis material image data again from the first line-integrated data and the second line-integrated data. As a result, the correcting unit 36c is able to obtain a corrected attenuation coefficient.

Figure 6:
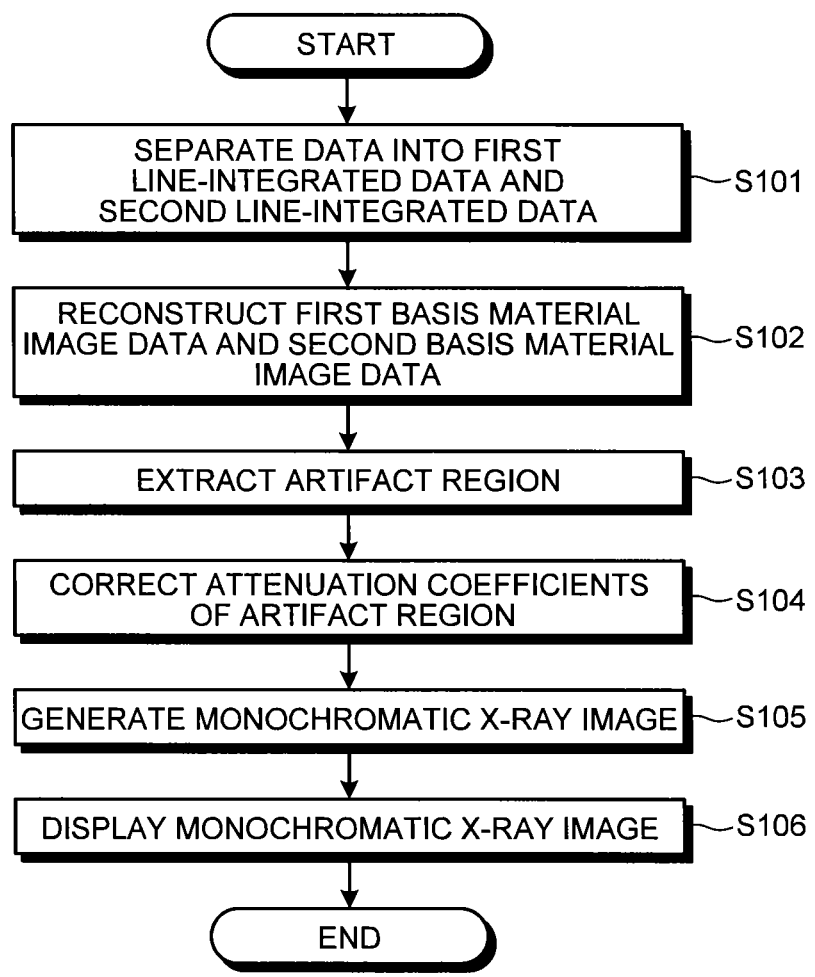
FIG. 6 is a flowchart of an exemplary processing performed by the X-ray CT apparatus according to the first embodiment.

Next, an exemplary processing performed by the X-ray CT apparatus according to the first embodiment will be explained, with reference to FIG. 6. FIG. 6 is a flowchart of the exemplary processing performed by the X-ray CT apparatus according to the first embodiment.

As shown in FIG. 6, the separating unit 34b included in the X-ray CT apparatus according to the first embodiment separates high energy projection data and low energy projection data that have been acquired into first line-integrated data and second line-integrated data (step S101). After that, the reconstructing unit 36a reconstructs first basis material image data and second basis material image data from the first line-integrated data and the second line-integrated data, respectively (step S102).

Subsequently, the extracting unit 36b extracts an artifact region on a basis of the attenuation coefficient of each of the pixels calculated from the first basis material image data and the second basis material image data (step S103), and the correcting unit 36c corrects the attenuation coefficients of the artifact region (step S104).

After that, the reconstructing unit 36a generates a monochromatic X-ray image by using the corrected attenuation coefficients (step S105). Subsequently, the display device 32 displays the monochromatic X-ray image (step S106), and the processing is ended.

As explained above, according to the first embodiment, such a pixel of which the value of the attenuation coefficient calculated from the basis material image data exhibits a physical contradiction is extracted as the artifact region. As a result, according to the first embodiment, it is possible to extract the artifacts occurring in the monochromatic X-ray image. Furthermore, according to the first embodiment, the attenuation coefficients of the artifact region are corrected, so that the monochromatic X-ray image is generated by using the corrected attenuation coefficients. In other words, according to the first embodiment, it is possible to correct the weighting coefficients used for generating the monochromatic X-ray image. As a result, according to the first embodiment, it is possible to reduce the artifacts in the monochromatic X-ray image.

(Second Embodiment)

As a second embodiment, another embodiment related to methods for extracting an artifact region implemented by the extracting unit 36b will be explained. The artifact region extracting method explained in the first embodiment will be referred to as a first extracting method, whereas the artifact region extracting methods implemented by the extracting unit 36b according to the second embodiment will be described while being roughly divided into second to sixth extracting methods.

The second extracting method utilizes the notion that it is physically impossible for an attenuation coefficient to be 0 or smaller. According to the second extracting method, the extracting unit 36b extracts such pixels of which the attenuation coefficients are 0 or smaller as the artifact region. The energy range used for the extraction is set on a basis of the first basis material and the second basis material that have been set and within a range of X-ray tube voltages which the X-ray CT apparatus is capable of applying. In the following sections, the exemplary embodiment is explained in a case the energy range is set as "$E_a$ to $E_b$".

For example, the extracting unit 36b sequentially calculates attenuation coefficients within the range of "$E_a$ to $E_b$", on a basis of "$c_1$" and "$c_2$" of each of the pixels and Expression (1). After that, the extracting unit 36b extracts such a pixel that has a set made up of "$c_1$" and "$c_2$" from which an attenuation coefficient of 0 or smaller is calculated within the range of "$E_a$ to $E_b$", as an artifact region. According to this method, however, it is necessary to calculate all the attenuation coefficients within the range of "$E_a$ to $E_b$". Thus, to reduce the load of the extracting processing, in the second extracting method, in a case a set made up of "$c_1$" and "$c_2$" at one pixel satisfies either of the three conditions, the pixel is extracted as an artifact region: The first condition is that both of the values of "$c_1$" and "$c_2$" are 0 or smaller;

The second condition is that the value "$c_1$" is a negative value, and also Expression (5) shown below is satisfied where "R" denotes the maximum value of "$\mu_2(E)/\mu_1(E)$" within the range of "$E_a$ to $E_b$";

$$|c_1| \geq R \times |c_2| \tag{5}$$

The third condition is that the value "$c_2$" is a negative value, and also Expression (6) shown below is satisfied where "R'" denotes the maximum value of "$\mu_1(E)/\mu_2(E)$" within the range of "$E_a$ to $E_b$".

$$|c_2| \geq R' \times |c_1| \tag{6}$$

The values of "$c_1$" and "$c_2$" are known for each of all the pixels, and also, "R" and "R'" are known. Thus, according to the second extracting method, it is possible to reduce the load of the extracting processing by making a judgment using the first to the third conditions.

Next, the third extracting method and the fourth extracting method will be explained. According to the third and the fourth extracting methods, the extracting unit 36b extracts the artifact region by comparing each of the attenuation coefficients at a predetermined energy level with attenuation coefficients of materials that are set in advance at the predetermined energy level. In this situation, the predetermined energy level will be expressed as "E'". The value "E'" may be set by the operator or may be determined in an initial setting.

According to the third extracting method, a material (a "maximum absorption material") of which the absorption of X-rays that can be present in a human body is at the maximum serves as the material described above that is set in advance. According to the third extracting method, the extracting unit 36b extracts such a pixel of which the set made up of "$c_1$" and "$c_2$" satisfies the following condition: an attenuation coefficient "$\mu(E')$" at "E'" calculated by using Expression (1) is larger than the attenuation coefficient of the maximum absorption material at "E'", as an artifact region.

According to the fourth extracting method, a material (a "minimum absorption material") of which the absorption of X-rays that can be present in a human body is at the minimum serves as the material described above that is set in advance. According to the fourth extracting method, the extracting unit 36b extracts such a pixel of which the set made up of "$c_1$" and "$c_2$" satisfies the following condition: an attenuation coefficient "$\mu(E')$" at "$E'$" calculated by using Expression (1) is smaller than the attenuation coefficient of the minimum absorption material at "$E'$", as an artifact region.

Next, the fifth extracting method and the sixth extracting method will be explained. According to the fifth and the sixth extracting methods, the extracting unit 36b extracts the artifact region by comparing a ratio between attenuation coefficients at two mutually-different energy levels with a ratio between attenuation coefficients of a material that is set in advance at the two mutually-different energy levels. In this situation, the two mutually-different energy levels will be referred to as "$E_3$ and $E_4$, where $E_3<E_4$". The values of "$E_3$ and $E_4$" may be set by the operator or may be determined in an initial setting.

According to the fifth extracting method, the maximum absorption material serves as the material described above that is set in advance. According to the fifth extracting method, the extracting unit 36b calculates a ratio "$\mu(E_3)/\mu(E_4)$" between the attenuation coefficient "$\mu(E_3)$" at "$E_3$" and the attenuation coefficient "$\mu(E_4)$" at "$E_4$" that are calculated by using Expression (1). Furthermore, the extracting unit 36b obtains a ratio "$\mu_a(E_3)/\mu_a(E_4)$" between the attenuation coefficient "$\mu_a(E_3)$" at "$E_3$" and the attenuation coefficient "$\mu_a(E_4)$" at "$E_4$" of the maximum absorption material. After that, the extracting unit 36b extracts such a pixel of which the set made up of "$c_1$" and "$c_2$" satisfies the following condition: the ratio "$\mu(E_3)/\mu(E_4)$" is larger than the ratio "$\mu_a(E_3)/\mu a(E_4)$", as an artifact region.

According to the sixth extracting method, the minimum absorption material serves as the material described above that is set in advance. According to the sixth extracting method, the extracting unit 36b calculates a ratio "$\mu(E_3)/\mu(E_4)$" between the attenuation coefficient "$\mu(E_3)$" at "$E_3$" and the attenuation coefficient "$\mu(E_4)$" at "$E_4$" that are calculated by using Expression (1). Furthermore, the extracting unit 36b obtains a ratio "$\mu_b(E_3)/\mu_b(E_4)$" between the attenuation coefficient "$\mu_b(E_3)$" at "$E_3$" and the attenuation coefficient "$\mu_b(E_4)$" at "$E_4$" of the minimum absorption material. After that, the extracting unit 36b extracts such a pixel of which the set made up of "$c_1$" and "$c_2$" satisfies the following condition: the ratio "$\mu(E_3)/\mu(E_4)$" is smaller than the ratio "$\mu_b(E_3)\mu_b(E_4)$", as an artifact region.

Each of the first to the sixth extracting methods may be implemented solely. Alternatively, two or more of these extracting methods may be implemented in combination. By implementing two or more of the first to the sixth extracting methods in combination, it is possible to improve the level of precision of the artifact region extracting process. The correcting processing and the monochromatic X-ray image generating processing described in the first embodiment are also performed after the artifact region is extracted by using any of the methods described in the second embodiment.

(Third Embodiment)

As a third embodiment, a method for further improving the level of precision of the artifact region extracting processing performed by the extracting unit 36b will be explained.

When implementing any of the first to the sixth extracting methods, the extracting unit 36b according to the third embodiment ensures that, as a seventh extracting method, such a pixel of which pixel values in a mutually same position in the pieces of basis material image data each of which corresponds to a different one of the plurality of basis materials fall in a predetermined range is excluded from a target to be extracted as the artifact region. For example, the extracting unit 36b determines that such a pixel of which the values of "$c_1$" and "$c_2$" are both in the range of "$0\pm\alpha$" should be excluded from the target of the extraction. In this situation, the value "$\alpha$" may be set by the operator or may be determined in an initial setting.

According to the third embodiment, as a result of implementing the seventh extracting method, it is possible to avoid the situation where regions of air are extracted as noise.

Furthermore, when implementing any of the first to the sixth extracting methods, the extracting unit 36b according to the third embodiment may implement an eighth extracting method described below either together with or without the seventh extracting method.

When implementing the eighth extracting method, the extracting unit 36b according to the third embodiment extracts the artifact region from data obtained after a filtering processing is performed on the pieces of basis material image data each of which corresponds to a different one of the plurality of basis materials. For example, after a filtering processing such as one that uses a median filter is performed on the pieces of basis material image data, the extracting unit 36b extracts an artifact region. In this situation, the filtering processing may be performed by a processing unit other than the extracting unit 36b.

According to the third embodiment, by implementing the eighth extracting method, it is possible to eliminate isolated points caused by noise in the basis material image data.

(Fourth Embodiment)

Figure 7A:
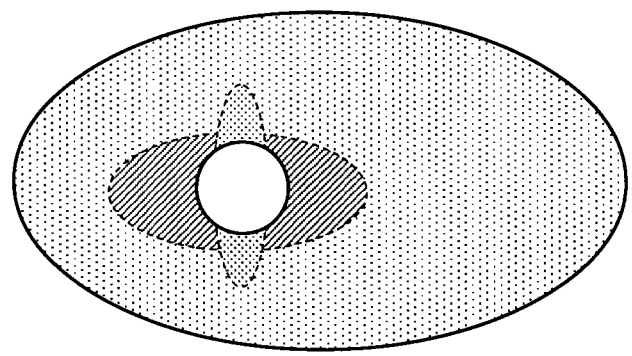
FIG. 7A and FIG. 7B are drawings for explaining a fourth embodiment.
Figure 7B:
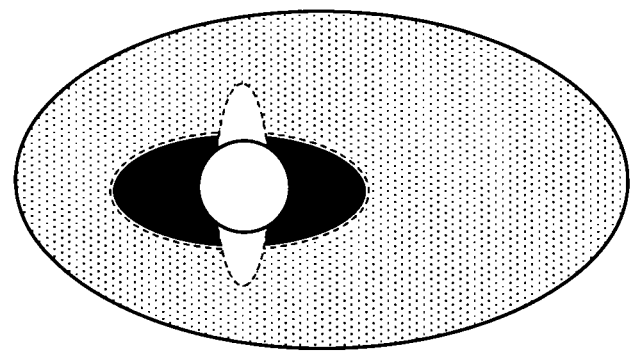

As a fourth embodiment, an example in which the artifact region extracted by the extracting unit 36b is indicated to a viewer will be explained with reference to FIGS. 7A and 7B. FIGS. 7A and 7B are drawings for explaining the fourth embodiment.

In the fourth embodiment, the system controlling unit 38 exercises control so that the artifact region is displayed while being emphasized within the monochromatic X-ray image using the corrected attenuation coefficients. For example, under the control of the system controlling unit 38, the reconstructing unit 36a renders, with a broken line, a contour of the artifact region within the monochromatic X-ray image using the corrected attenuation coefficients, as shown in FIG. 7A. After that, the display device 32 displays an image as shown in FIG. 7A under the control of the system controlling unit 38.

Alternatively, in the fourth embodiment, the system controlling unit 38 exercises control so that the artifact region is displayed while being emphasized within a monochromatic X-ray image using the attenuation coefficients before the correction. For example, under the control of the system controlling unit 38, the reconstructing unit 36a renders, with a broken line, a contour of the artifact region within the monochromatic X-ray image using the pre-correction attenuation coefficients, as shown in FIG. 7B. After that, the display device 32 displays an image as shown in FIG. 7B under the control of the system controlling unit 38.

In this situation, the system controlling unit 38 may exercise control so that a monochromatic X-ray image in which the extracted artifact region is colored is displayed.

Also, in the fourth embodiment, when the artifact region is displayed while being emphasized within the monochromatic X-ray image using the pre-correction attenuation coefficients, the attenuation coefficient correcting processing by the correcting unit 36c may be omitted.

In the fourth embodiment, because the artifact region within the monochromatic X-ray image is visualized, it is possible to present, for example, any region that has a possibility of missing information due to highly-absorbent materials, to an interpreting doctor who interprets the monochromatic X-ray image.

The medical image processing methods explained above in the first to the fourth embodiments are also applicable to a situation where a "multi-energy image taking processing" is performed while using three or more mutually-different levels of X-ray tube voltages. Furthermore, the medical image processing methods explained above in the first to the fourth embodiments are also applicable to a situation where three or more basis materials are set.

In the first to the fourth embodiments described above, the examples are explained in which the X-ray detector 13 is an integral-type detector. However, the medical image processing methods explained above in the first to the fourth embodiments are also applicable to a situation where the X-ray detector 13 is a photon-counting-type detector that individually counts the light originated from the X-rays that have passed through the subject P. When the X-ray detector 13 is a detector of a photon-counting-type, the separating unit 34b is able to calculate a linear attenuation coefficient from projection data acquired by performing an image taking processing while the X-ray tube voltage is fixed to one level.

Furthermore, the medical image processing methods described above in the first to the fourth embodiments may be implemented by another medical image processing apparatus that is separately installed in addition to the X-ray CT apparatus. In that situation, the medical image processing apparatus receives the projection data acquired by the X-ray CT apparatus and implements any of the medical image processing methods described above.

Furthermore, the constituent elements of the apparatuses and the devices that are shown in the drawings are based on functional concepts. Thus, it is not necessary to physically configure the elements as indicated in the drawings. In other words, the specific mode of distribution and integration of the apparatuses and the devices is not limited to the ones shown in the drawings. It is acceptable to functionally or physically distribute or integrate all or a part of the apparatuses and the devices in any arbitrary units, depending on various loads and the status of use. Furthermore, all or an arbitrary part of the processing functions performed by the apparatuses and the devices may be realized by a Central Processing Unit (CPU) and a computer program that is analyzed and executed by the CPU or may be realized as hardware using wired logic.

As explained above, according to at least one aspect of the first to the fourth embodiments, it is possible to extract the artifacts occurring in the monochromatic X-ray image.

While certain embodiments of the present invention have been described, these embodiments have been presented by way of examples only, and are not intended to limit the scope of the inventions. These exemplary embodiments may be embodied in a variety of other forms; furthermore, various omissions, substitutions, and changes may be made without departing from the spirit of the inventions. The inventions defined in the accompanying claims and their equivalents are intended to cover various embodiments and modifications, in the same manner as those embodiments and modifications would fall within the scope and spirit of the inventions.

What is claimed is:

1. A medical image processing apparatus comprising: processing circuitry that separates projection data into pieces of line-integrated data each of which corresponds to a different one of a plurality of basis materials that are set in advance, reconstructs pieces of basis material image data from the pieces of line-integrated data each of which corresponds to a different one of the plurality of basis materials, the pieces of basis material image data being configured so that each pixel value of each of pixels indicates an abundance ratio of corresponding each of the basis materials that is present at each of the pixel, extracts an artifact region, on a basis of attenuation coefficients of each of the pixels calculated from the pieces of basis material image data each of which corresponds to a different one of the plurality of basis materials, and corrects the attenuation coefficients at the artifact region, wherein the processing circuitry generates a monochromatic X-ray image by using the corrected attenuation coefficients.

2. The medical image processing apparatus according to claim 1, wherein the processing circuitry obtains an energy level at which each of the attenuation coefficients of the artifact region calculated from pixel values in the pieces of basis material image data each of which corresponds to a different one of the plurality of basis materials exhibits a correct value, and performs a correcting processing by using each of the attenuation coefficients of the artifact region at the obtained energy level and attenuation coefficients of predetermined materials at the obtained energy level.

3. The medical image processing apparatus according to claim 2, wherein the processing circuitry obtains a value calculated in advance as the energy level at which each of the attenuation coefficients of the artifact region exhibits the correct value, the attenuation coefficients being calculated from the pixel values in the pieces of basis material image data each of which corresponds to a different one of the plurality of basis materials.

4. The medical image processing apparatus according to claim 1, wherein the processing circuitry performs a correcting processing by replacing each of the attenuation coefficients of the artifact region with attenuation coefficients of predetermined materials.

5. The medical image processing apparatus according to claim 1, wherein the processing circuitry extracts the artifact region from data obtained after a filtering processing is performed on the pieces of basis material image data each of which corresponds to a different one of the plurality of basis materials.

6. The medical image processing apparatus according to claim 1, wherein the processing circuitry extracts the artifact region by comparing attenuation coefficients at two mutually-different energy levels with each other, within an energy range that does not include absorption edge energies.

7. The medical image processing apparatus according to claim 1, wherein the processing circuitry extracts such a pixel of which the attenuation coefficients are 0 or smaller as the artifact region.

8. The medical image processing apparatus according to claim 1, wherein the processing circuitry extracts the artifact region by comparing each of the attenuation coefficients at a predetermined energy level with attenuation coefficients of materials that are set in advance at the predetermined energy level.

9. The medical image processing apparatus according to claim 1, wherein the processing circuitry extracts the artifact region by comparing a ratio between attenuation coefficients at two mutually-different energy levels with a ratio between attenuation coefficients of a material that is set in advance at the two mutually-different energy levels.

10. The medical image processing apparatus according to claim 1, wherein the processing circuitry ensures that such a pixel of which pixel values in a mutually same position in the pieces of basis material image data each of which corresponds to a different one of the plurality of basis materials fall in a predetermined range is excluded from a target to be extracted as the artifact region.

11. The medical image processing apparatus according to claim 1, wherein the projection data is represented by two pieces of projection data acquired by using two mutually-different levels of X-ray tube voltages.

12. The medical image processing apparatus according to claim 1, wherein the processing circuitry exercises control so that the artifact region is displayed while being emphasized within the monochromatic X-ray image using the corrected attenuation coefficients or a monochromatic X-ray image using the attenuation coefficients before the correction.

13. An X-ray computed tomography apparatus comprising:
   a detector configured to detect X-rays having passed through a subject; and
   processing circuitry configured to
      separate projection data generated based on a detection signal of the detector into pieces of line-integrated data each of which corresponds to a different one of a plurality of basis materials that are set in advance,
      reconstruct pieces of basis material image data from the pieces of line-integrated data each of which corresponds to a different one of the plurality of basis materials, the pieces of basis material image data being configured so that each pixel value of each of pixels indicates an abundance ratio of corresponding each of the basis materials that is present at each of the pixel,
      extract an artifact region, on a basis of attenuation coefficients of each of the pixels calculated from the pieces of basis material image data each of which corresponds to a different one of the plurality of basis materials, and
      correct the attenuation coefficients at the artifact region, wherein
   the processing circuitry is further configured to generate a monochromatic X-ray image by using the corrected attenuation coefficients.

* * * * *